United States Patent
Lu

(10) Patent No.: US 6,654,639 B1
(45) Date of Patent: Nov. 25, 2003

(54) METHOD AND DEVICE FOR MULTI-CHAMBER CARDIAC PACING IN RESPONSE TO A TACHYCARDIA

(75) Inventor: Richard Lu, Thousand Oaks, CA (US)

(73) Assignee: Pacesetter, Inc., Sylmar, CA (US)

( * ) Notice: Subject to any disclaimer, the term of this patent is extended or adjusted under 35 U.S.C. 154(b) by 264 days.

(21) Appl. No.: 09/850,560

(22) Filed: May 7, 2001

(51) Int. Cl.⁷ ............................................. A61N 1/365
(52) U.S. Cl. ......................................... 607/17; 607/14
(58) Field of Search .............................. 607/4, 5, 9, 14

(56) References Cited

U.S. PATENT DOCUMENTS

| | | | |
|---|---|---|---|
| 4,712,555 A | 12/1987 | Thornander et al. | 128/419 PG |
| 4,788,980 A | 12/1988 | Mann et al. | 128/419 PG |
| 4,809,697 A | 3/1989 | Causey, III et al. | 128/419 PT |
| 4,940,052 A | 7/1990 | Mann et al. | 128/419 PG |
| 4,944,298 A | 7/1990 | Sholder | 128/419 PG |
| 4,944,299 A | 7/1990 | Silvian | 128/419 PG |
| 5,024,222 A * | 6/1991 | Thacker | 607/22 |
| 5,144,947 A | 9/1992 | Wilson | 128/419 PG |
| 5,466,254 A | 11/1995 | Helland | 607/123 |
| 5,573,550 A | 11/1996 | Zadeh et al. | 607/28 |
| 5,685,315 A | 11/1997 | McClure et al. | 128/708 |
| 5,720,768 A * | 2/1998 | Verboven-Nelissen | 607/9 |
| 5,991,656 A * | 11/1999 | Olson et al. | 607/4 |
| 6,308,095 B1 * | 10/2001 | Hsu et al. | 600/518 |
| 6,370,427 B1 * | 4/2002 | Alt et al. | 607/4 |
| 6,442,429 B1 * | 8/2002 | Hill et al. | 607/14 |

OTHER PUBLICATIONS

Krater, Leon et al., "Effect of Antitachycardia Pacing (ATP) Location on the Efficacy of Ventricular Tachycardia Termination", PACE, Poster Presented, Abstract Attached, Apr. 2001, vol. 24, No. 4, Part II, p. 485.

St. Jude Medical; "SVT Discrimination with the Photon™ DR ICD", Twice as TACHY, Tachycardia Educational Series, pp: 1–8 (TAT #5).

* cited by examiner

Primary Examiner—George R. Evanisko

(57) ABSTRACT

An apparatus and method for performing multi-chamber anti-tachycardia pacing (ATP) in response to a tachycardia that is of particular use in an implantable cardiac stimulation device. The expected benefits of such a multi-chamber ATP include improved hemodynamic performance and the ability to terminate the tachycardia sooner. Embodiments of the present invention use an intrinsic chamber activation sequence and associated interchamber time delays, preferably automatically detected during a period of time when a pathologic tachycardia is not present, to treat a pathologic tachycardia should it occur. Such a device monitors two or more chambers of the patient's heart, i.e., the controlled chambers, and in the event a tachycardia is detected, the device determines the chamber which originated the tachycardia. The device then calculates anti-tachycardia pacing (ATP) cycle lengths, typically as percentages of the detected tachycardia cycle length of the chamber where the tachycardia originated, and begins pacing the controlled chambers according to the intrinsic chamber activation sequence and interchamber delays (initially synchronized relative to a cardiac signal from the chamber which originated the tachycardia) at the ATP cycle lengths for a predefined period or until the tachycardia ends. Optionally, embodiments of the present invention may additionally include a hemodynamic sensor and may adaptively alter the activation sequence and/or interchamber time delays in response to feedback from the hemodynamic sensor.

24 Claims, 10 Drawing Sheets

METHOD AND DEVICE FOR MULTI-CHAMBER CARDIAC PACING IN RESPONSE TO A TACHYCARDIA

FIELD OF THE INVENTION

The present invention is generally directed to an implantable medical device, e.g., a cardiac stimulation device, and is particularly directed to a method for treating tachycardia in a multi-chamber cardiac stimulation device.

BACKGROUND OF THE INVENTION

Implantable cardiac stimulation devices are well known in the art. They include implantable pacemakers which provide stimulation pulses to cause a heart, which may beat too slowly or at an irregular rate, to beat at a controlled normal rate. They also include defibrillators, which detect when the atria and/or the ventricles of the heart are in fibrillation or a pathologic tachycardia and apply cardioverting or defibrillating electrical energy to the heart to restore the heart to a normal rhythm. Implantable cardiac stimulation devices may also include the combined functions of a pacemaker and a defibrillator.

The treatment and avoidance of ventricular fibrillation, is significant since without needed treatment, death may occur within minutes of an episode's onset. It is estimated that such "sudden cardiac death" may result in 350,000 to 450,000 people per year, approximately one every minute. Tachycardia, i.e., an elevated cardiac rate typically in excess of 100 bpm (beats per minute), while potentially being symptomatic to the patient is generally not fatal. However, a tachycardia episode may accelerate either directly or via progression of the disease process into fibrillation and death may result. Therefore, it is desirable and potentially necessary to treat a tachycardia episode to avoid such a fatal progression.

While cardioversion or defibrillation therapy can be used, devices that can do such therapy, e.g., implantable cardioverter defibrillators (ICDs), are generally larger, costlier, and have shorter operational lives due to a larger power consumption. Additionally, the pain to the patient will generally be significant if the patient is awake. Accordingly, even with an ICD, a lower voltage, "painless" treatment referred to as anti-tachycardia pacing (ATP) may be used, at least as a first stage treatment. With ATP, one or more pacing pulses (typically a train of pacing pulses) are applied to a single chamber, typically the right ventricle or right atrium, where the tachycardia is sensed. The ATP pulses are generally applied synchronous to the detected tachycardia and at an accelerated rate. This type of treatment has been shown to be effective of terminating the tachycardia episode. However, should this single chamber ATP fail, treatment may need to be accelerated to cardioversion or defibrillation.

While cardiac stimulators, i.e., pacemakers and ICDs, with dual chamber, i.e., right atrium and right ventricle, sensing and pacing capabilities are well known, it is only in recent years that the industry has begun exploring devices that could sense and pace three or four chambers of the patient's heart. However, it is believed that this exploration has not addressed the consequences of the use of such devices in treating tachycardia.

Therefore, what is needed is a system that can provide an improved ATP technique for treating a tachycardia that is suitable for a multi-chamber environment.

SUMMARY OF THE INVENTION

The present invention provides an improved system and method for performing multi-chamber anti-tachycardia pacing (ATP) in response to a tachycardia that is of particular use in an implantable cardiac stimulation device. The expected benefits of such a multi-chamber ATP include improved hemodynamic performance and the ability to terminate the tachycardia sooner. Embodiments of the present invention use an intrinsic chamber activation sequence and associated interchamber time delays, preferably automatically detected during a period of time when a pathologic tachycardia is not present, to treat a pathologic tachycardia should it occur. Such a device monitors two or more chambers of the patient's heart, i.e., the controlled chambers, and in the event a tachycardia is detected, the device determines the chamber which originated the tachycardia. The device then selects an anti-tachycardia pacing (ATP) cycle length, typically a percentage of the detected tachycardia cycle length of the chamber where the tachycardia originated, and begins pacing the controlled chambers according to the intrinsic chamber activation sequence and interchamber delays (initially synchronized relative to a cardiac signal from the chamber which originated the tachycardia) at the ATP cycle length for a predefined period or until the tachycardia ends. Optionally, embodiments of the present invention may additionally include a hemodynamic sensor and may adaptively alter the activation sequence and/or interchamber time delays in response to feedback from the hemodynamic sensor.

A preferred implantable cardiac stimulation device configured for controlling a plurality of chambers of a patient's heart through a plurality of electrodes implanted in electrical contact with each of the controlled chambers is comprised of a plurality of pulse generators (i.e., pacing circuits) each respectively configured for electrical coupling to at least one of the electrodes and configured to generate stimulation pulses to stimulate an associated chamber; a plurality of sensing circuits each respectively configured for electrical coupling to at least one of the electrodes and configured to receive intrinsic cardiac signals from an associated chamber; and a controller, coupled to the pulse generators and the sensing circuits, for detecting the presence of tachycardia from the received intrinsic signals and for determining which one of the chambers originated the tachycardia. When the controller detects tachycardia, a sequence of stimulation pulses is delivered according to calculated anti-tachycardia pacing cycle lengths to the controlled chambers relative to an intrinsic chamber activation sequence and associated interchamber time delays.

In a further aspect of the present invention, at least the initial delivery of the stimulation pulse sequence is synchronized relative to the chamber which originated the tachycardia, i.e., if the left atrium originated the tachycardia, then the left atrial pulse of the stimulation pulse sequence would be timed relative to the last intrinsic pulse that occurred in the originating chamber, i.e., the left atrium in this example.

In a next aspect of a preferred embodiment of the present invention, the intrinsic chamber activation sequence is periodically determined during periods of time when a pathologic tachycardia is not detected in any of the sensed chambers. When the stimulation pulse sequence is applied to terminate the tachycardia, it is preferably applied at an accelerated rate to attempt to terminate the tachycardia.

In a still further aspect of the present invention, a hemodynamic monitor may be used to monitor the performance of the patient's heart in response to the aforedescribed therapy. While the therapy progresses, the applied activation sequence and/or its associated interchamber delays are adaptively modified in response to the output of the hemodynamic monitor to improve the heart's performance during delivery of the aforedescribed therapy.

The novel features of the invention are set forth with particularity in the appended claims. The invention will be best understood from the following description when read in conjunction with the accompanying drawings.

DETAILED DESCRIPTION OF THE PREFERRED EMBODIMENTS

The following description is of the best mode presently contemplated for carrying out the invention. This description is not to be taken in a limiting sense, but is made merely for the purpose of describing the general principles of the invention. The scope of the invention should be determined with reference to the claims.

The present invention provides an improved apparatus and method for treating tachycardia with an implantable cardiac stimulation device, e.g., a pacemaker or an implantable cardioverter/defibrillator (ICD).

Figure 1:
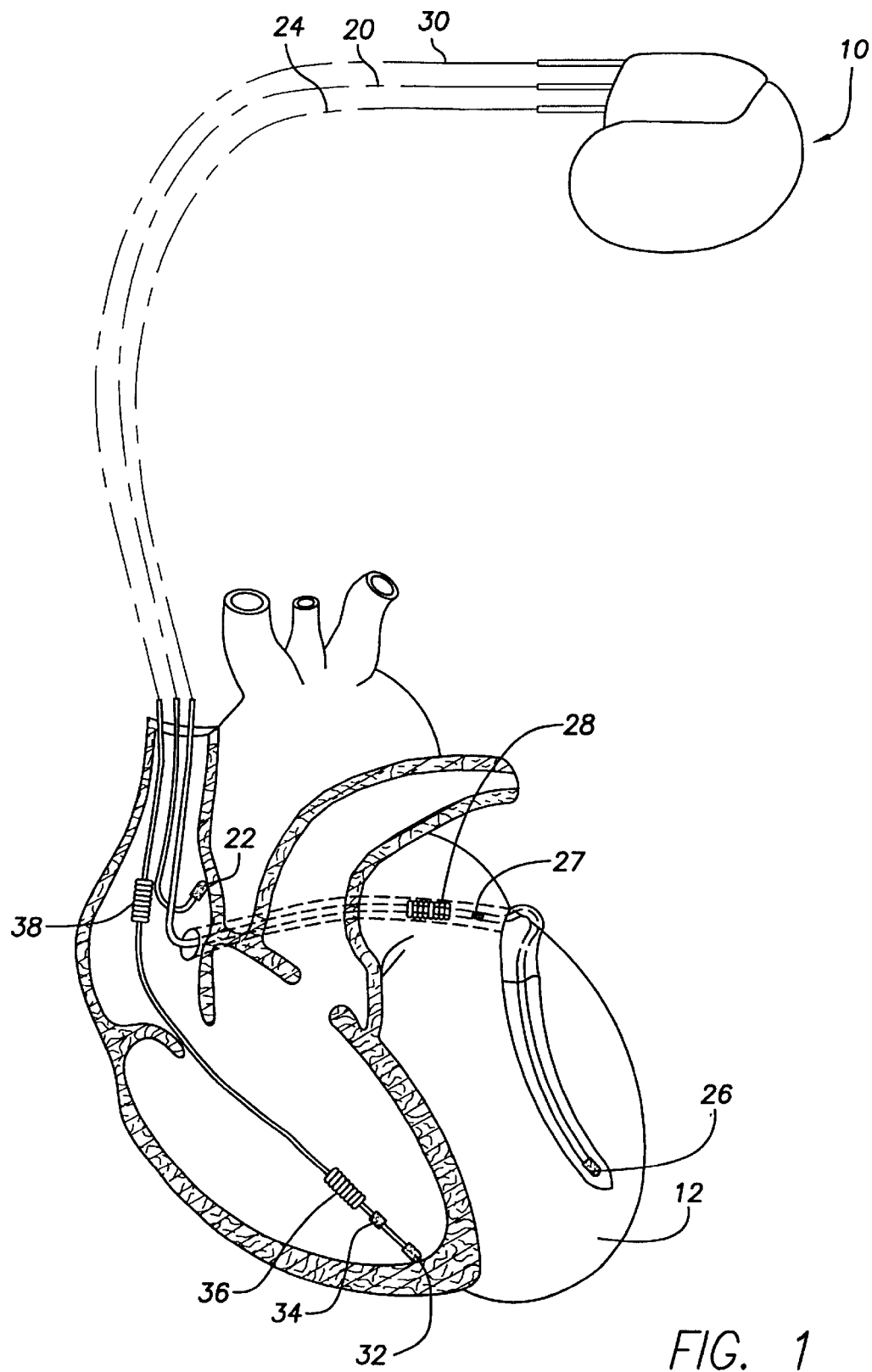
FIG. 1 is a simplified diagram illustrating an implantable stimulation device in electrical communication with at least three leads implanted into a patient's heart for delivering multi-chamber stimulation and shock therapy.

As shown in FIG. 1, there is a stimulation device 10 in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left chamber pacing therapy, the stimulation device 10 is coupled to a "coronary sinus" lead 24 designed for placement in the "coronary sinus region" via the coronary sinus os for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28. For a complete description of a coronary sinus lead,. see U.S. patent application Ser. No. 09/196,898, "A Self-Anchoring Coronary Sinus Lead" (Pianca et al.), and U.S. Pat. No. 5,466,254, "Coronary. Sinus Lead with Atrial Sensing Capability" (Helland), which patents are hereby incorporated herein by reference.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode 36 will be positioned in the right ventricle and the SVC coil electrode 38 will be positioned in the superior vena cava. Accordingly, the right ventricular lead 30 is capable of receiving cardiac signals and delivering stimulation in the form of pacing and shock therapy to the right ventricle.

Figure 2:
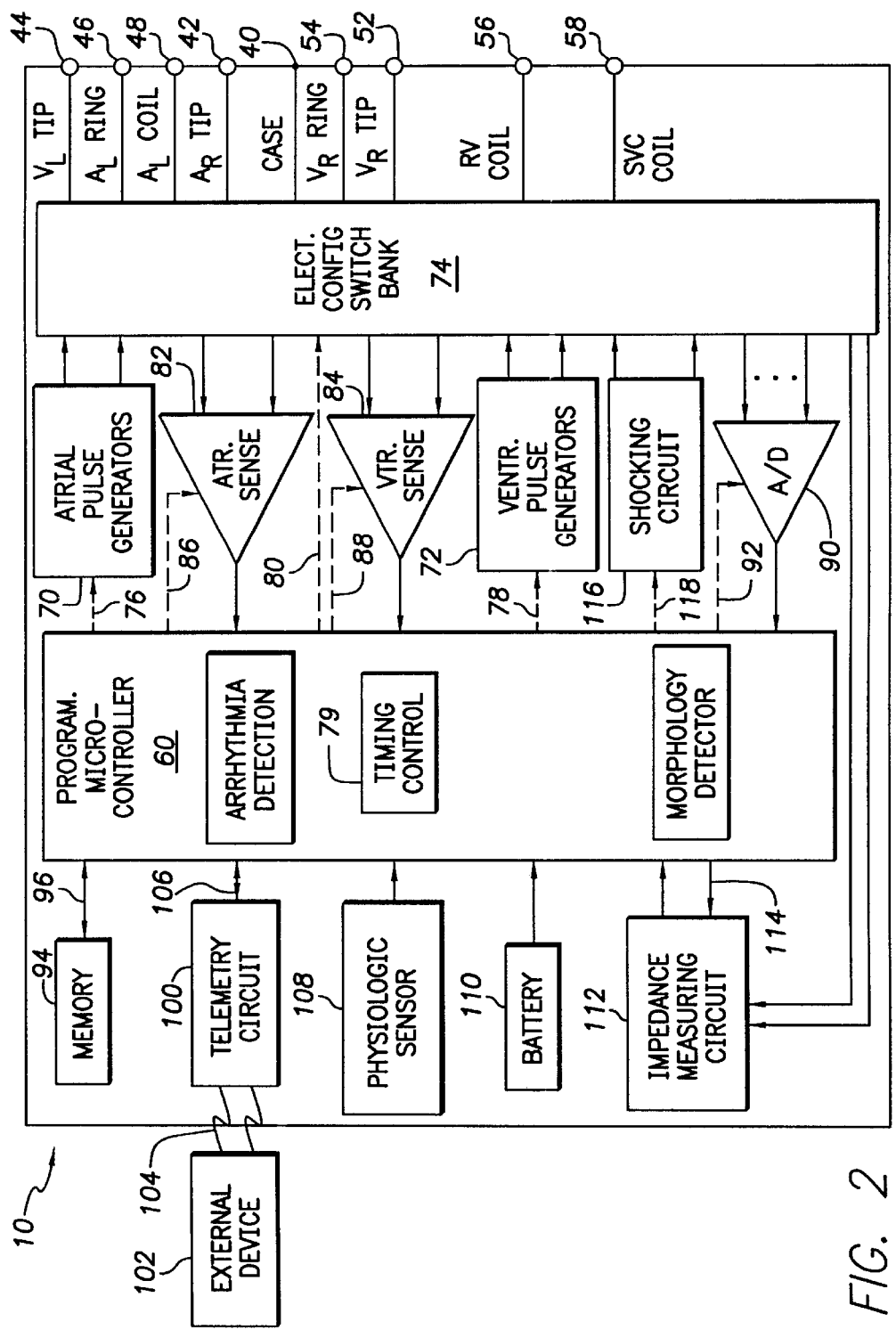
FIG. 2 is a functional block diagram of a multi-chamber implantable stimulation device illustrating the basic elements of a stimulation device which can provide cardioversion, defibrillation and pacing stimulation in four chambers of the heart.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the right atrial tip electrode 22.

To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular ring electrode 26, the left atrial ring electrode 27, and the left atrial coil electrode 28, respectively.

To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 which controls the various modes of stimulation therapy. As is well known in the art, the microcontroller 60 typically includes a microprocessor, or equivalent control circuitry or processor, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions are well known in the art.

Representative types of control circuitry that may be used with the invention include the microprocessor-based control system of U.S. Pat. No. 4,940,052 (Mann et al.) and the state-machine of U.S. Pat. No. 4,712,555 (Sholder) and U.S. Pat. No. 4,944,298 (Sholder). For a more detailed description of the various timing intervals used within the stimulation device and their inter-relationships, see U.S. Pat. No. 4,788,980 (Mann et al.). The '052, '555, '298 and '980 patents are incorporated herein by reference.

As shown in FIG. 2, atrial pulse generators 70 and ventricular pulse generators 72 generate pacing stimulation pulses for delivery by the right atrial lead 20, the right ventricular lead 30, and/or the coronary sinus lead 24 via an electrical configuration switch bank 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A—A) delay, or ventricular interconduction (V—V) delay, etc.) as well as to keep track of the timing of refractory periods, PVARP intervals, noise detection windows, evoked response windows, alert intervals, marker channel timing, etc., which is well known in the art.

The switch bank 74 includes a plurality of switches for connecting the desired electrodes to the appropriate I/O circuits, thereby providing complete electrode programmability. Accordingly, the switch bank 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch bank 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch bank 74 determines the "sensing polarity" of the cardiac signal by selectively closing the appropriate switches, as is also known in the art. In this way, the clinician may program the sensing polarity independent of the stimulation polarity.

Each of the sensing circuits, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. For a complete description of a typical sensing circuit, see U.S. Pat. No. 5,573,550, entitled "Implantable Stimulation Device having a Low Noise, Low Power, Precision Amplifier for Amplifying Cardiac Signals" (Zadeh et al.). For a complete description of an automatic gain control system, see U.S. Pat. No. 5,685,315, entitled "Cardiac Arrhythmia Detection System for an Implantable Stimulation Device" (McClure et al.). Accordingly, the '550 and the '315 patents are hereby incorporated herein by reference. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart. The sensing circuits, 82 and 84, in turn, receive control signals over signal lines, 86 and 88, from the microcontroller 60 for purposes of controlling the gain, threshold, polarization charge removal circuitry (not shown), and the timing of any blocking circuitry (not shown) coupled to the inputs of the sensing circuits, 82 and 84, as is known in the art.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (e.g., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch bank 74 to sample cardiac signals across any pair of desired electrodes.

Advantageously, the data acquisition system 90 may be coupled to the microcontroller 60, or other detection circuitry, for detecting an evoked response from the heart 12 in response to an applied stimulus, thereby aiding in the detection of "capture". Capture occurs when an electrical stimulus applied to the heart is of sufficient energy to depolarize the cardiac tissue, thereby causing the heart muscle to contract. The microcontroller 60 detects a depolarization signal during a window following a stimulation pulse, the presence of which indicates that capture has occurred. The microcontroller 60 may enable capture detection by triggering the ventricular pulse generator 72 or atrial pulse generator 70 to generate a stimulation pulse, starting a capture detection window using the timing control circuitry 79 within the microcontroller 60, and enabling the data acquisition system 90 via control signal 92 to sample the cardiac signal that falls in the capture detection window and, based on the amplitude, determines if capture has occurred.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy. A feature of the present invention is the ability to sense and store a relatively large amount of data (e.g., from the data acquisition system 90), which data may then be used for subsequent analysis to guide the programming of the device.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104. For examples of such devices, see U.S. Pat. No. 4,809,697, entitled "Interactive Programming and Diagnostic System for use with Implantable Pacemaker" (Causey, III et al.); U.S. Pat. No. 4,944,299, entitled "High Speed Digital Telemetry System for Implantable Device" (Silvian); and U.S. patent application Ser. No. 09/223,422, filed Dec. 12, 1998, entitled "Efficient Generation of Sensing Signals in an Implantable Medical Device such as a Pacemaker or ICD" (McClure et al.), which patents are hereby incorporated herein by reference.

In the preferred embodiment, the stimulation device 10 further includes a physiologic sensor 108, commonly referred to as a "rate responsive" sensor because it is typically used to adjust pacing stimulation rate according to the exercise state of the patient. However, the physiologic sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V—V Delay, etc.) at which the atrial and ventricular pulse generators, 70 and 72, generate stimulation pulses. While shown as being included within the stimulation device 10, it is to be understood that the physiologic sensor 108 may also be external to the stimulation device 10, yet still be implanted within or carried by the patient. A common type of rate responsive sensor is an activity sensor, such as an accelerometer or a piezoelectric crystal, which is mounted within the housing 40 of the stimulation device 10. Other types of physiologic sensors are also known, for example, sensors which sense the oxygen content of blood, respiration rate and/or minute ventilation, pH of blood, ventricular gradient, etc. However, any sensor may be used which is capable of sensing a physiological parameter which corresponds to the exercise state of the patient. The type of sensor used is not critical to the present invention and is shown only for completeness.

The stimulation device additionally includes a battery 110 which provides operating power to all of the circuits shown in FIG. 2. For the stimulation device 10, which employs shocking therapy, the battery 110 must be capable of operating at low current drains for long periods of time (preferably less than 10 $\mu$A), and then be capable of providing high-current pulses (for capacitor charging) when the patient requires a shock pulse (preferably, in excess of 2 A for periods of 10 seconds or more). The battery 110 must also have a predictable discharge characteristic so that elective replacement time can be detected. Accordingly, the device 10 preferably employs lithium/silver vanadium oxide batteries, as is true for most (if not all) current devices.

The stimulation device 10 further includes magnet detection circuitry (not shown) coupled to the microcontroller 60. It is the purpose of the magnet detection circuitry to detect when a magnet is placed over the stimulation device 10, which magnet may be used by a clinician to perform various test functions of the stimulation device 10 and/or to signal the microcontroller 60 that the external programmer 102 is in place to receive or transmit data to the microcontroller 60 through the telemetry circuits 100.

As further shown in FIG. 2, the device 10 is shown as having an impedance measuring circuit 112 which is enabled by the microcontroller 60 via a control signal 114. The known uses for an impedance measuring circuit 112 include, but are not limited to, lead impedance surveillance during the acute and chronic phases for proper lead positioning or dislodgment; detecting operable electrodes and automatically switching to an operable pair if dislodgment occurs; measuring respiration or minute ventilation; measuring thoracic impedance for determining shock thresholds; detecting when the device has been implanted; measuring stroke volume; and detecting the opening of heart valves, etc. The impedance measuring circuit 112 is advantageously coupled to the switch bank 74 so that any desired electrode may be used. The impedance measuring circuit 112 is not critical to the present invention and is shown only for completeness.

In the case where the stimulation device 10 is intended to operate as an implantable cardioverter/defibrillator (ICD) device, it must detect the occurrence of an arrhythmia and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 joules), moderate (0.5–10 joules) or high energy (10–40 joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and synchronized with an R-wave and/or pertaining to the treatment of tachycardia. Defibrillation shocks are generally of moderate to high energy level (i.e., corresponding to thresholds in the range of 0.5–40 joules), delivered asynchronously (since R-waves or P-waves may be too disorganized) and pertaining exclusively to the treatment of fibrillation. Accordingly, the microcontroller 60 is capable of controlling the synchronous or asynchronous delivery of the shocking pulses.

Figure 3:
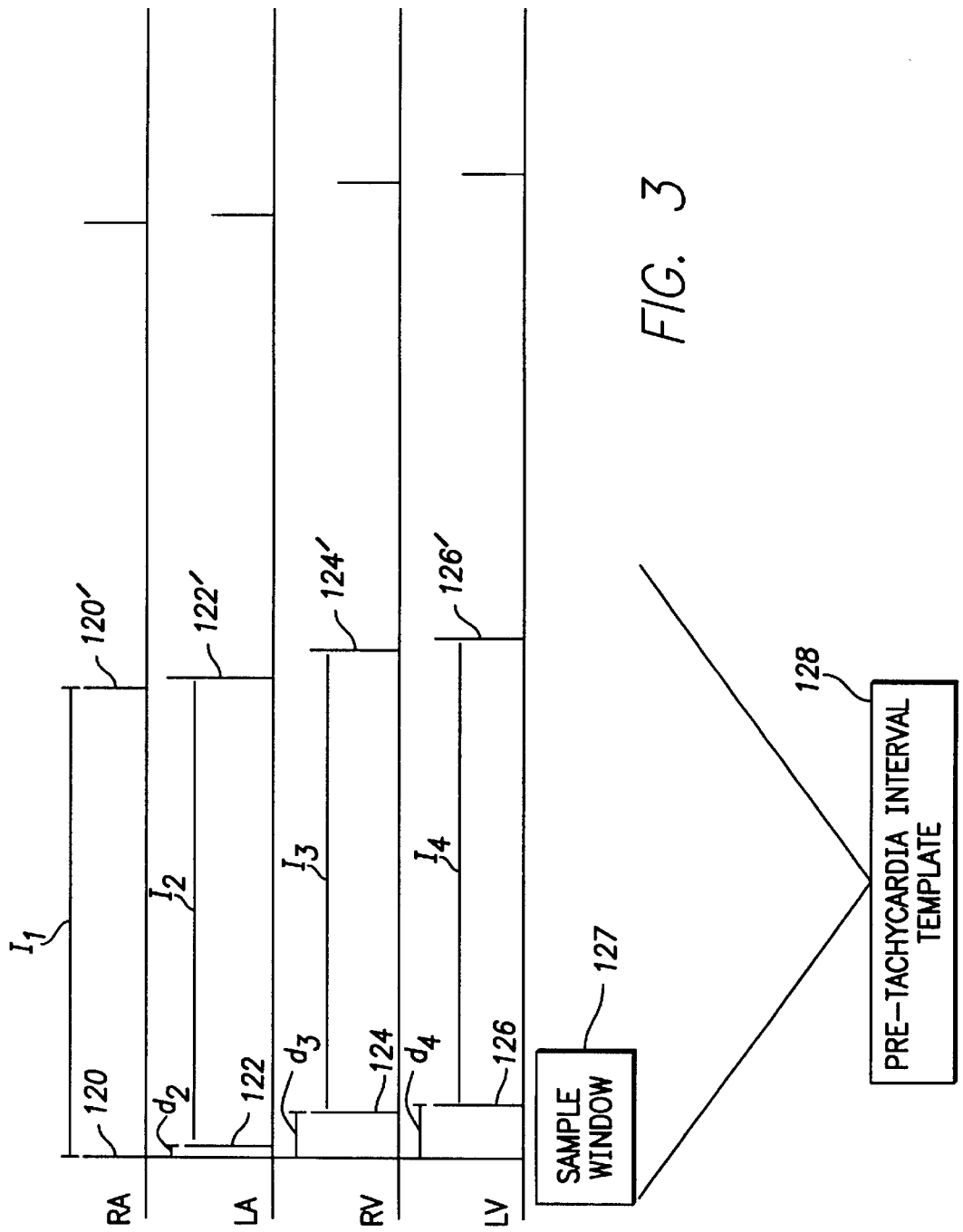
FIG. 3 shows a simplified timing diagram of the intrinsic signals present in each of the four chambers of a patient's heart during a period of time when a pathologic tachycardia is not present. The present invention samples the intrinsic signals to determine an interval template.
Figure 4:
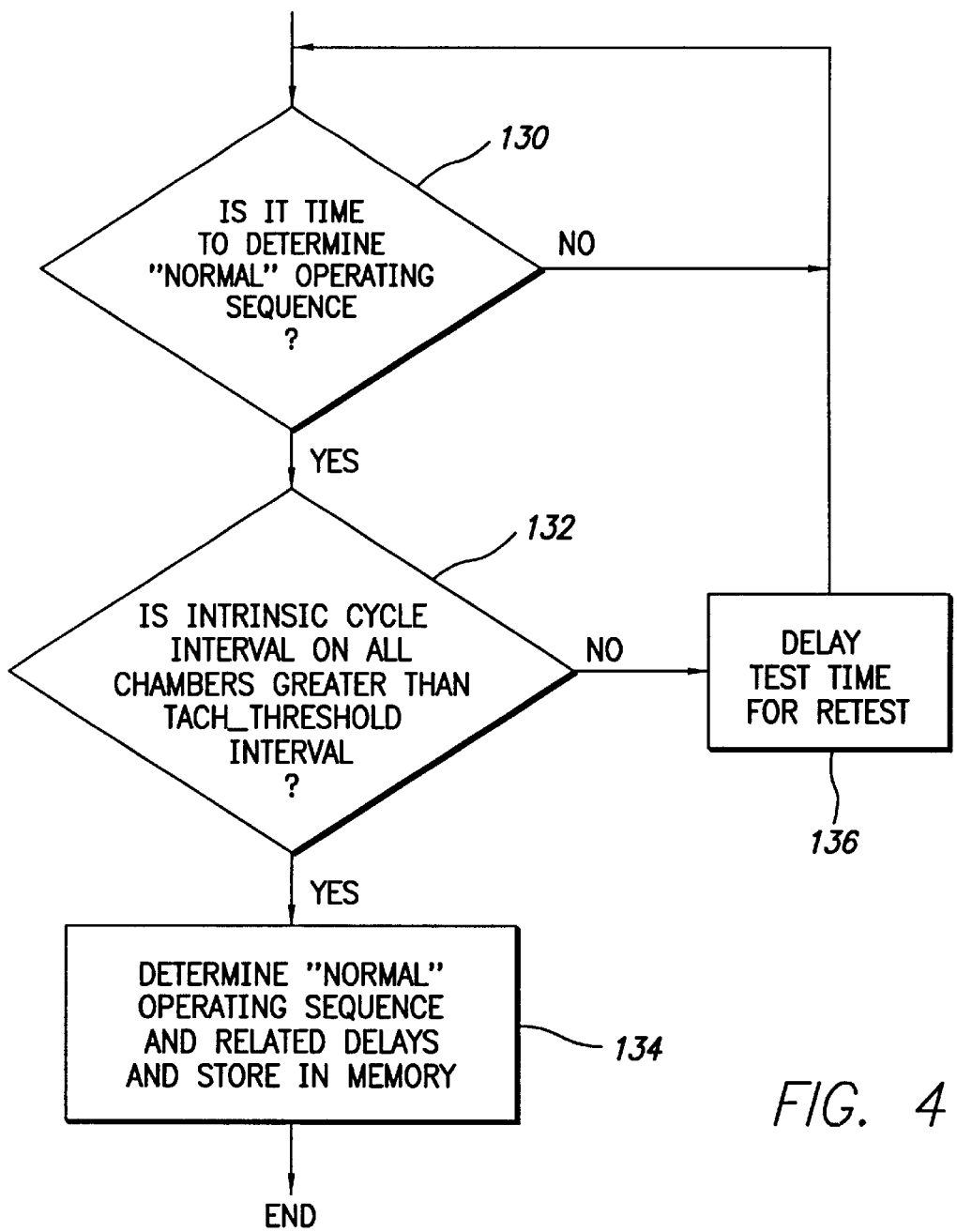
FIG. 4 shows a simplified flow chart of an exemplary process used for determining the (pre-tachycardia) interval template from the exemplary intrinsic signals of FIG. 3.

FIG. 3 shows a simplified timing diagram of the intrinsic signals present in each of the four chambers of a patient's heart during a period of time when pathologic tachycardia is not present. The present invention preferably samples the intrinsic signals to determine a (pre-tachycardia) interval template that is subsequently adjusted for use as a pacing template for treating tachycardia. FIG. 4 shows a simplified flow chart of the process for determining the interval template from the exemplary intrinsic signals of FIG. 3 and ensuring that the interval template is representative of the "normal" (i.e., non-tachycardia) interchamber cardiac cycle timing. The present invention primarily relates to the timing of the interchamber signals and the derivation of a multi-chamber activation sequence of pacing signals, e.g., an anti-tachycardia pacing (ATP) sequence that can be used by the implantable cardiac stimulation device 10 to terminate a detected tachycardia. As such, the referenced timing diagrams only show simplified intrinsic signals (timing marks) that are representative of the timing of the depolarization/repolarization signals that are sensed by the atrial and ventricular sense amplifiers, 82, 84, and/or the intracardiac electrogram (IEGM) signals sensed by the data acquisition system 90 of the present device. It is recognized that these vertical timing marks only represent the signal timing and not the shape of these intrinsic signals. Additionally, while the attached figures describe a multi-chamber system that independently monitors and controls four chambers of the heart, i.e., the right atrium, the left atrium, the right ventricle, and the left ventricle, the present invention is equally applicable to any multi-chamber, e.g., a two or three chamber, system or a multi-site system.

In a normally operating heart, the activation of the chambers of the heart begins with a signal from the sinoatrial (SA) node. The SA node causes depolarizations and associated contractions of each of the chambers of the patient's heart through well-known conduction paths, i.e., the AV node, the right and left bundle branches, the Purkinje fibers, etc. Due to the structure of the conduction system of a normally operating heart, the depolarization and the associated intrinsic electrical signals occur with the right atrium (where the SA node is located) contracting first, followed shortly by contraction of the left atrium. Contraction of the ventricles in a normal heart is delayed from the contraction of the atria by the AV node to allow for filling of the ventricles and thus improves the hemodynamics of the heart. As with the atria, there is typically a nominal delay between the contraction of the right ventricle and the left ventricle.

As shown in FIG. 3, the right atrial depolarization signal 120, precedes the left atrial depolarization signal 122, which precedes the right ventricular depolarization signal 124, which precedes the left ventricular depolarization signal 126. Relative to the right atrial pulse 120, the left atrial pulse 122 is delayed by a delay period $d_2$. Relative to the right atrial pulse 120, the right ventricular pulse 124 is delayed by a delay period $d_3$. Relative to the right atrial pulse 120, the left ventricular pulse 126 is delayed by a delay period $d_4$. In an exemplary heart at a nominal heart rate, e.g., 80 beats per minute (bpm), the $d_2$, $d_3$, $d_4$ delays are 10, 70 and 80 milliseconds, respectively. As described further below, the microcontroller 60 preferably determines these interchamber delays by sampling the intrinsic cardiac signals for each of the monitored chambers during a sample window period 127 selected to be of sufficient duration, e.g., 300 milliseconds, to sense each of the cardiac signals, 120, 122, 124, and 126.

Additionally characteristic of the intrinsic cardiac sequence is the interval between intrinsic cardiac signals in each of the chambers. In FIG. 3, these intervals are designated as $I_1$, for the interval between cardiac signals in the right atrium (120–120'), $I_2$ for the interval between cardiac signals in the left atrium (122–122'), $I_3$ as the interval between cardiac signals in the right ventricle (124–124'), and $I_4$ as the interval between cardiac signals in the left ventricle (126–126'). Typically, in the absence of tachycardia or other atypical condition, the cardiac cycle intervals $I_1, I_2, I_3$, and $I_4$ are essentially the same. Typically, there is some amount of variation in consecutive cardiac cycle intervals. Accordingly, embodiments of the present invention preferably accommodate these variations, e.g., by averaging a plurality of interval measurements from each chamber in determining the stored interval values.

The sensed information is stored (as described further in reference to FIG. 9) as an interval template 128, measured during a time period without pathologic tachycardia. An exemplary procedure for determining the interval template 128 is shown in FIG. 4. In step 130, the microcontroller 60 periodically determines whether it is time to determine the "normal" intrinsic operating sequence. This determination can be made according to one or more of the following exemplary criteria: (1) a time period, e.g., every 24 hours, or (2) the patient being in a sleep state or position, e.g., according to heart rate, accelerometer, inclinometer criteria, etc. If it is determined in step 130 that the test should proceed, the cardiac cycle intervals, e.g., $I_1$, $I_2$, $I_3$, $I_4$, are examined in step 132 for each of the monitored chambers. In step 132, each of the measured cardiac cycle intervals is compare to a predetermined tachycardia threshold ($tach_{13}$ threshold) interval criteria, e.g., 500 milliseconds corresponding to a cardiac cycle rate of 120 bpm. If it is determined in step 132 that the patient's heart is operating in a normal operating range, i.e., none of the chambers are experiencing a pathologic tachycardia, the interval template 128 is measured by the microcontroller 60 in step 134 as previously described in reference to FIG. 3. Otherwise, the process proceeds to step 136 where a retest of step 130 is delayed by a prescribed time period.

In the case of an AV block, the intrinsic depolarizations of the ventricles will have little relationship to the atrial depolarizations. Accordingly, the measured $d_3$, $d_4$ delays will have little meaning. Accordingly in such a case, default values are preferably used for the $d_3$, $d_4$ delays. Similar accommodations are made when a bundle branch block is present.

Figure 5:
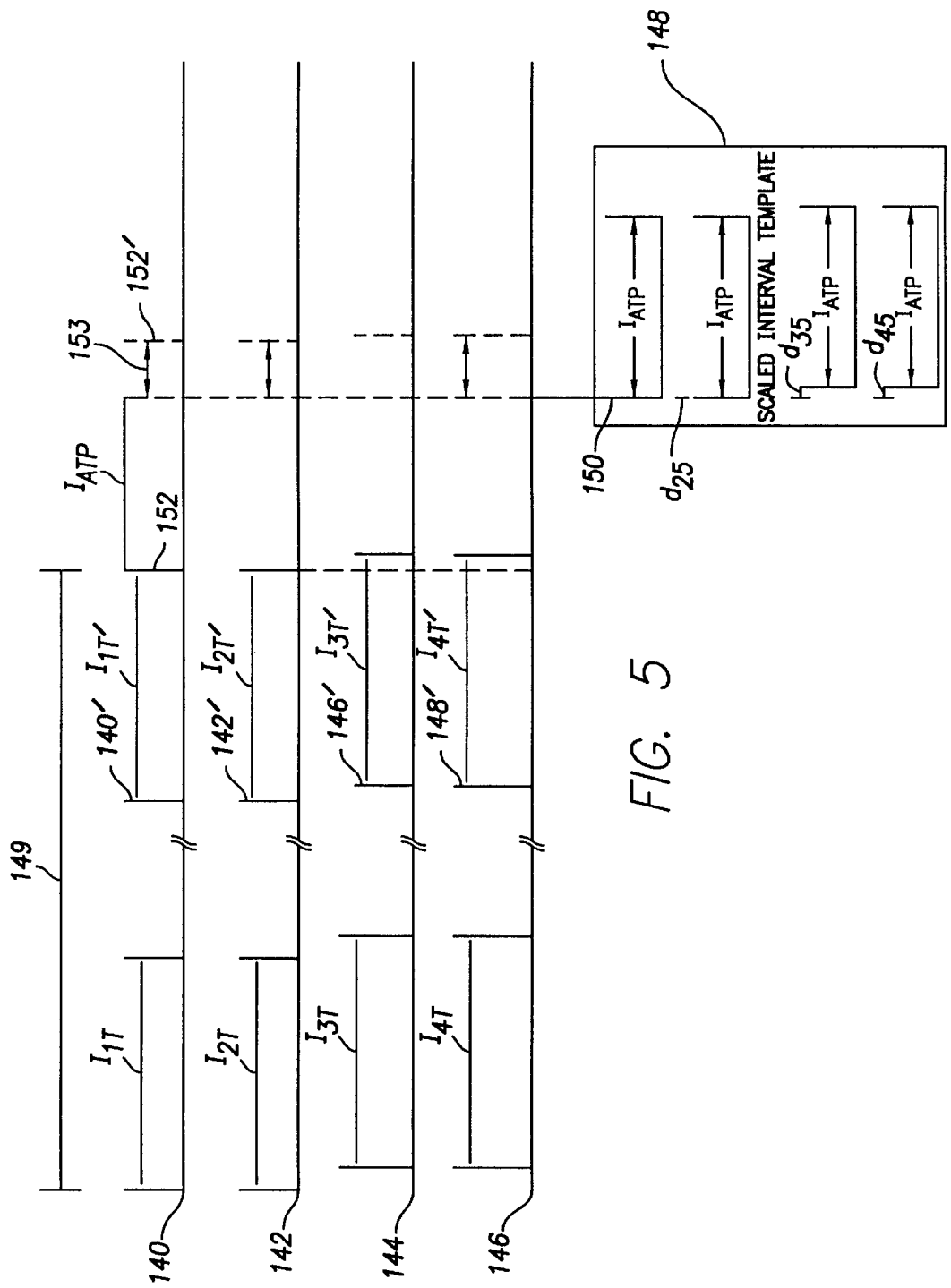
FIG. 5 shows a simplified timing diagram of the intrinsic signals present in each of the four chambers of a patient's heart during a period of tachycardia. In the present example, the tachycardia originates in the right atrium and is terminated by scaling the interval template and synchronizing the delivery of the scaled interval template to the originating chamber.

FIG. 5 shows a simplified timing diagram of the intrinsic signals 140, 142, 144, 146, present in each of the four chambers of a patient's heart 12 during a period of pathologic tachycardia. In a preferred embodiment, the tachycardia originates in the right atrium and is subsequently terminated by scaling the interval template 128 and synchronizing the delivery of a scaled interval template 148 relative to the originating chamber. For example, in FIG. 5 the tachycardia is shown at a rate of 150 bpm or a cardiac interval duration of 400 milliseconds. Typically, each cardiac interval duration, $I_{1T}$, $I_{2T}$, $I_{3T}$, and $I_{4T}$, is approximately the same as the tachycardia propagates from the originating chamber, e.g., the right atrium. When one or more of the cardiac cycle intervals is less than the predefined tach_threshold value, thus signifying the presence of tachycardia, the origin of the tachycardia can be determined by observing any differences in the cardiac interval durations and/or changes in the cardiac signal activation sequence, e.g., if the left atrial cardiac signal 142 precedes the right atrial cardiac signal 140, the origin of the tachycardia is typically the left atrium. In this example, we have assumed that the tachycardia originated in the right atrium since the cardiac cycle intervals, $I_{1T}$, $I_{2T}$, $I_{3T}$, and $I_{4T}$, are approximately the same duration and the cardiac signal sequence corresponds to its pre-tachycardia sequence.

Accordingly in a first mode of ATP therapy, an ATP sequence is determined by setting the ATP cardiac cycle duration $I_{ATP}$ to a percentage, e.g., 80%, of the tachycardia cycle length, e.g., $I_{1T}$, of the originating chamber, e.g., the right atrium, to generate the scaled interval template 148. Accordingly, $I_{ATP}$ is set to 320 milliseconds in this example, i.e., 80% of 400 milliseconds. By decreasing the tachycardia cycle length used in the ATP sequence, the pacing rate has increased, e.g., 320 milliseconds corresponds to 187.5 bpm. This interval $I_{ATP}$ may be used for each of the anti-tachycardia pacing intervals in the scaled interval template 148. Additionally, since the interchamber delays naturally decrease in a properly functioning heart, the measured interchamber delay periods, $d_2$, $d_3$, $d_4$, are preferably also adjusted downward (as discussed further below) to $d_{2s}$, $d_{3s}$, $d_{4s}$, in response to the pacing intervals.

This scaled interval template 148 is then used to stimulate the monitored chambers, e.g., the right atrium, the left atrium, the right ventricle and the left ventricle, of the patient's heart 12. Preferably, the scaled interval template 148 is synchronously applied relative to the intrinsic cardiac signal of the chamber, which originated the tachycardia, following confirmation that a tachycardia exists. Preferably, this confirmation consists of monitoring multiple cardiac cycles and observing a cardiac cycle interval indicative of tachycardia for X out of the last Y cardiac cycles, e.g., 2 out of the last 3 cardiac cycles. As shown, in FIG. 5, there may be a confirmation period 149 of multiple cardiac cycles (shown in part by the broken time axis) during which time period a tachycardia is confirmed. Finally, after the cardiac cycle with intrinsic depolarization signals 140'–146', X out of the last Y cardiac cycles have confirmed a tachycardia and an average interval duration is calculated.

Once the tachycardia has been confirmed during the confirmation period 149, the scaled pacing template is then applied at the ATP interval $I_{ATP}$ following the signal from the originating chamber if the originating chamber is the right atrium. If the originating chamber is not the right atrium, pacing will be applied according to the predetermined sequence and interchamber delays synchronized to the signal in the originating chamber. The scaled pacing template is initially synchronized (subject to a delay corresponding to the $I_{ATP}$ value) to the intrinsic signal from the tachycardia originating chamber. Accordingly, each of the pacing pulses delivered from the scaled pacing template will also proceed when the next intrinsic event would have occurred and will tend to terminate the tachycardia. Typically, this ATP pacing will comprise a train of multiple pacing pulses delivered related to the interval template 148.

For example, in this case, the first application of the first pulse 150, i.e., the right atrial pacing pulse, of the scaled interval template 148 is applied synchronous with the right atrial cardiac signal 152 at the aforementioned ATP interval $I_{ATP}$ and thus precedes when the next right atrial depolarization 152' would have occurred by interval 153, i.e., the difference between the average intrinsic tachycardia interval (e.g., the average of $I_{4T} \ldots I_{1T}$) for the right atrium and the ATP interval $I_{ATP}$.

Figure 6:
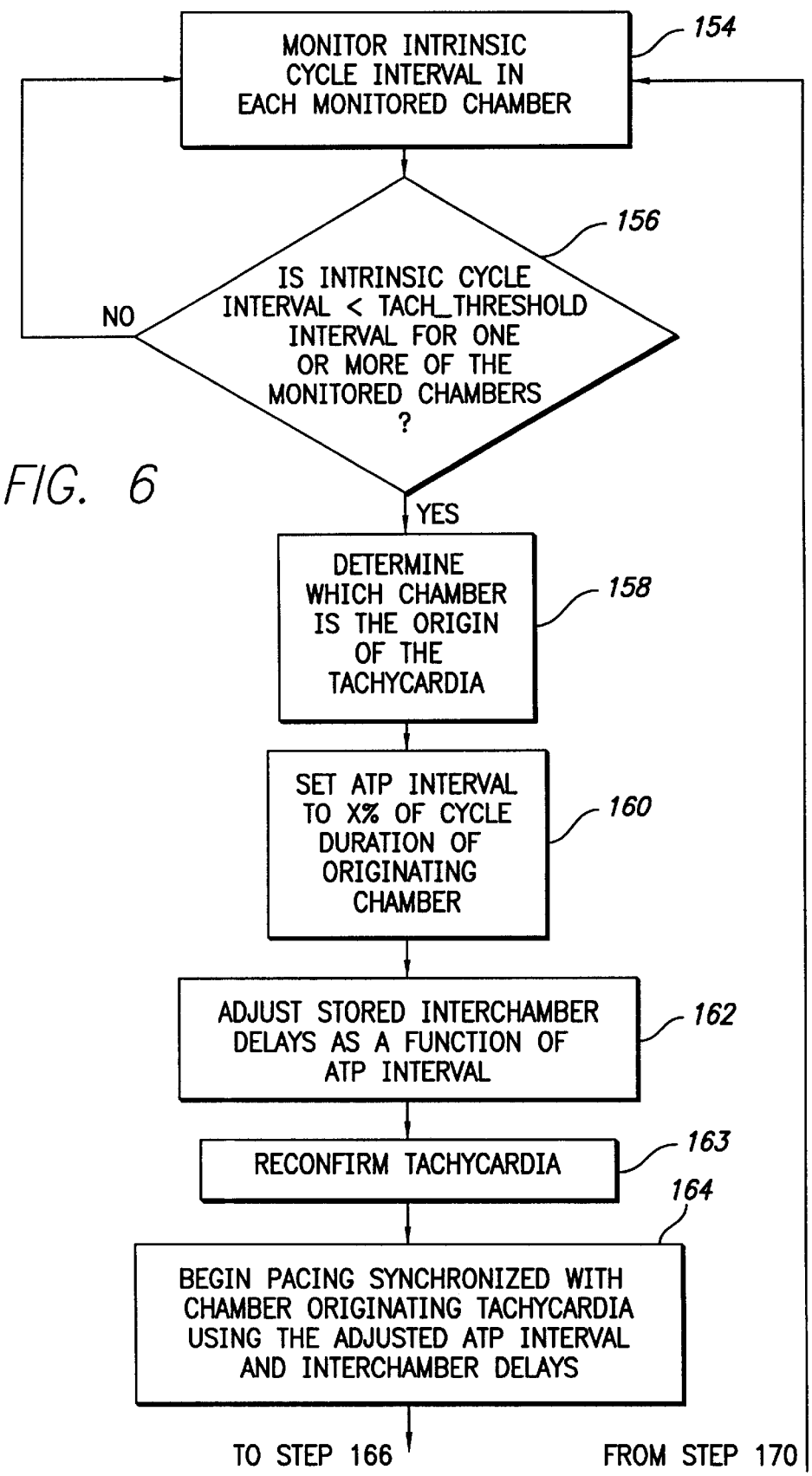
FIGS. 6 and 7 show a simplified flow chart of an exemplary process used for detecting and terminating the tachycardia of FIG. 5.
Figure 7:
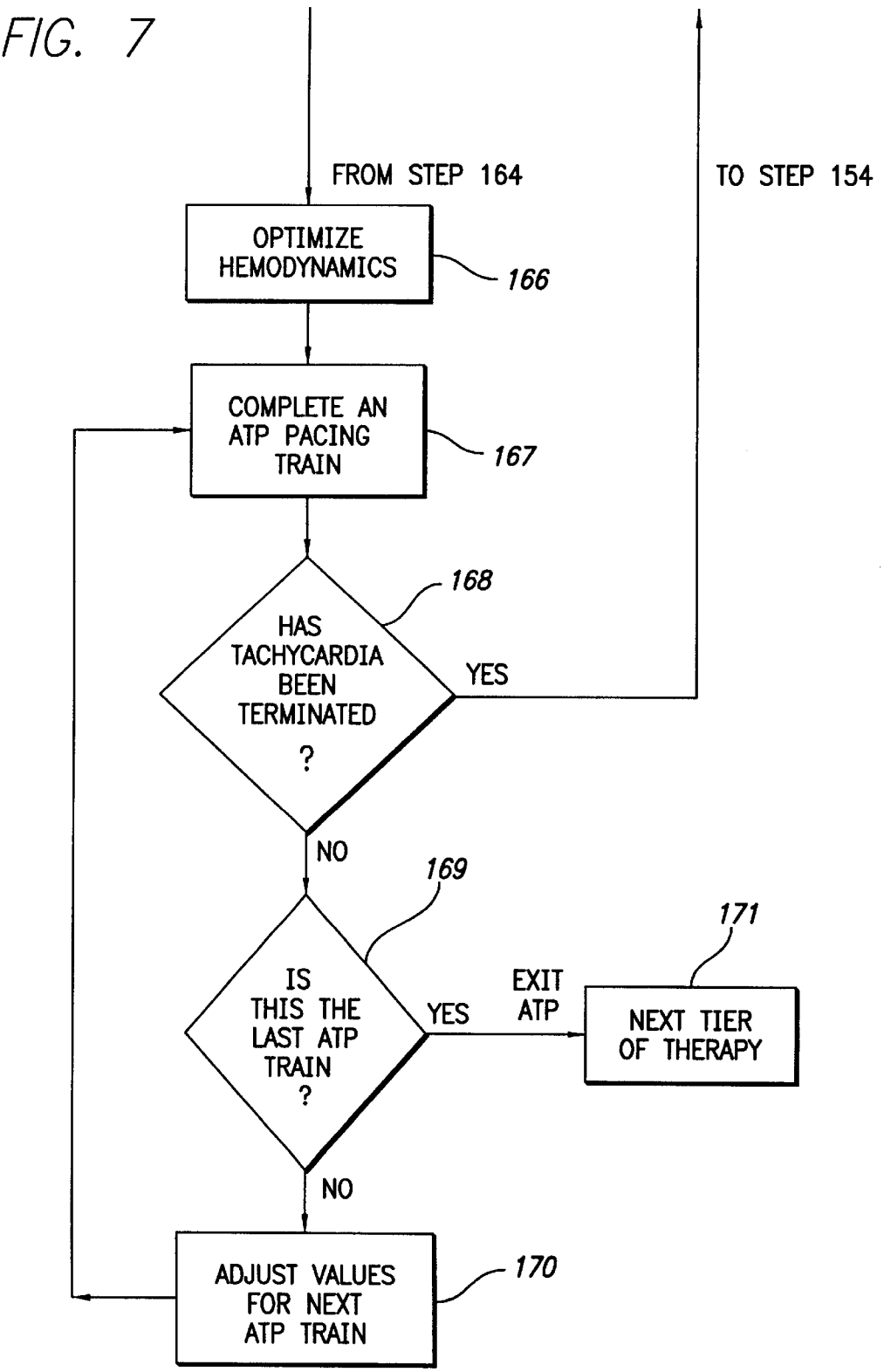

FIGS. 6 AND 7 show a simplified flow chart of an exemplary process used for detecting and terminating the tachycardia of FIG. 5. Initially, in steps 154 and 156, the microcontroller 60 monitors the intrinsic intervals, $I_{1T}$, $I_{2T}$, $I_{3T}$, and $I_{4T}$, to measure the interval durations and subsequently determine whether these intervals of one or more cycles are indicative of tachycardia by comparing these measured values to a predetermined tachycardia threshold (tach_threshold) interval value. This process repeats as a background operation until a tachycardia is detected. Next, in step 158, as described above, the chamber that originated the tachycardia is determined. The cardiac cycle interval and associated rate is determined from the originating chamber and the ATP interval duration, $I_{ATP}$, is preferably determined by taking a percentage, e.g., 80%, of the measured tachycardia interval. The timing intervals of the measured interval template 128 are scaled in step 160 according to the $I_{ATP}$ while maintaining the measure interchamber delays and this becomes the scaled interval template 148. Optionally, in step 162, the measured interchamber delays, $d_2$, $d_3$, and $d_4$ are also scaled, i.e., reduced, according to the ATP interval. This interchamber delay scaling function will be described further below in relation to FIGS. 5A and 5B.

In step 163, the presence of tachycardia is confirmed, e.g., if tachycardia is sensed in X out of the last Y cardiac cycles. In step 164, delivery of this scaled interval template begins, initially synchronized relative to the chamber that originated the tachycardia. Optionally, in step 166, as described in reference to FIGS. 10 AND 11, the characteristics of the scaled interval template 148 may be altered to optimize the hemodynamics of the patient's heart 12 during this treatment. After the scaled interval template has been delivered for a prescribed number of pacing cycles according to a prescribed ATP pacing train, as defined in step 167, it is determined in step 168 whether the tachycardia has been terminated. If the tachycardia has been terminated the process continues to step 154 where it monitors for a reoccurrence of a tachycardia. If the tachycardia has not been terminated, the process continues at step 169 where it is determined if the last designated type or variation of the ATP pacing train has been used. If variations are still available, a next variation is selected in step 170 and the process continues with step 167. For example, a variation may comprising altering the scaling percentage of step 160, the number of pacing pulses or the spacing of the pacing pulses applied according to the interval template, etc. If all of the designated ATP variations have been used, the process continues with step 171 where the next tier of therapy is used, e.g., cardioversion or defibrillation.

Figures 8, 9:
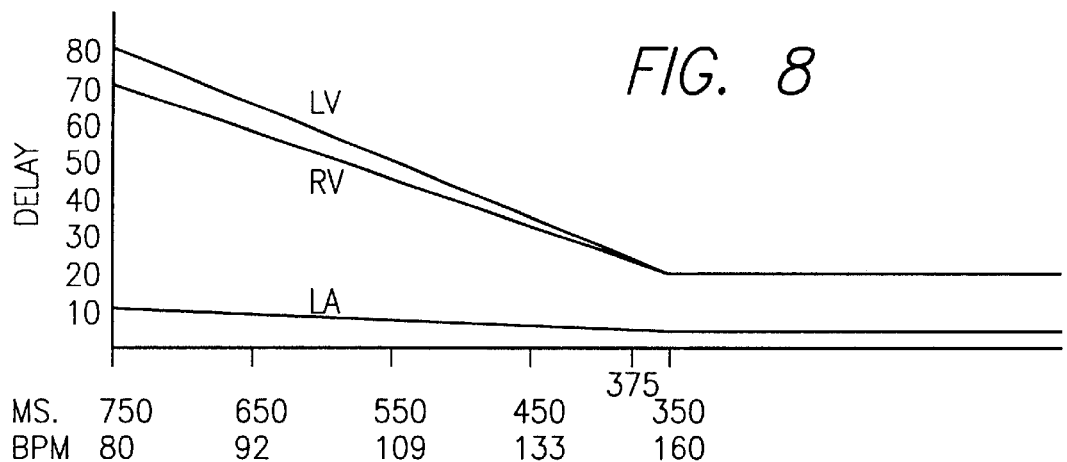
FIG. 8 shows an exemplary curve for adjusting the interchamber delays as a function of the cardiac cycle interval/rate.
FIG. 9 shows an exemplary table for storing parameters used for determining the interchamber delays shown in FIG. 8.

As described above in reference to step 162 of FIG. 6, the interchamber delays may be modified as a function of the determined $I_{ATP}$. Accordingly, FIG. 8 shows an exemplary curve for adjusting the interchamber delays as a function of the ATP cardiac cycle interval $I_{ATP}$ using the data stored in the exemplary table of FIG. 9. When the cardiac interval template 128 is measured in step 134 of FIG. 4, the cardiac cycle interval is also stored along with the interchamber delays $d_2$, $d_3$, and $d_4$. Preferably this data, $I_M$, $d_{2M}$, $d_{3M}$, $d_{4M}$, is stored in a table or equivalent data structure as shown in the table 172 of FIG. 9. As previously discussed, when tachycardia is not present, the cardiac cycle intervals $I_1$, $I_2$, $I_3$, $I_4$, are typically essentially the same. As such, only a single cardiac cycle interval $I_M$ need be stored in table 172. Optionally, the stored data may include (not shown) the associated cardiac cycle interval for each measured interchamber delay. Additionally, as previously discussed, it is noted that the interchamber delays decrease in a normal heart as the heart rate increases (or cardiac cycle interval decreases). Accordingly, data is preferably stored in table 172 that corresponds to a predetermined minimum interchamber delays $d_{2MIN}$, $d_{3MIN}$, $d_{4MIN}$, for a predetermined minimum cardiac cycle interval $I_{MIN}$. These predetermined minimum values may be preprogrammed into the device 10 as fixed and/or default values or may be programmable from the external device 102. It is recognized that the cardiac cycle interval may decrease further than this minimum value (and the associated cardiac cycle rate may increase further than the associated maximum rate). However, in this exemplary algorithm, the minimum interchamber delays are not allowed to decrease below these stored values, i.e., the interchamber delays "bottom out". In this exemplary algorithm, the adjustment is done in a linear manner as shown in the graph of FIG. 8. Accordingly, the interchamber delay is set to a value (before "bottoming out") defined by the equation:

$$I_d = d_{xM} - ((d_{xM} - d_{xMIN}) * (I_M - I_{ATP}))/(I_M - I_{MIN}))$$

where $d_{xM}$, $d_{xMIN}$, $I_M$ and $I_{MIN}$ are taken from the table of FIG. 9 and $I_{ATP}$ is the cardiac cycle interval for the chamber originating the tachycardia adjusted by a percentage as described above in reference to step 160 of FIG. 6. However, other algorithms or techniques, e.g., a table, may be used to adjust the interchamber delays as a function of the cardiac cycle rate and are considered to be within the scope of the present invention.

Figure 10:
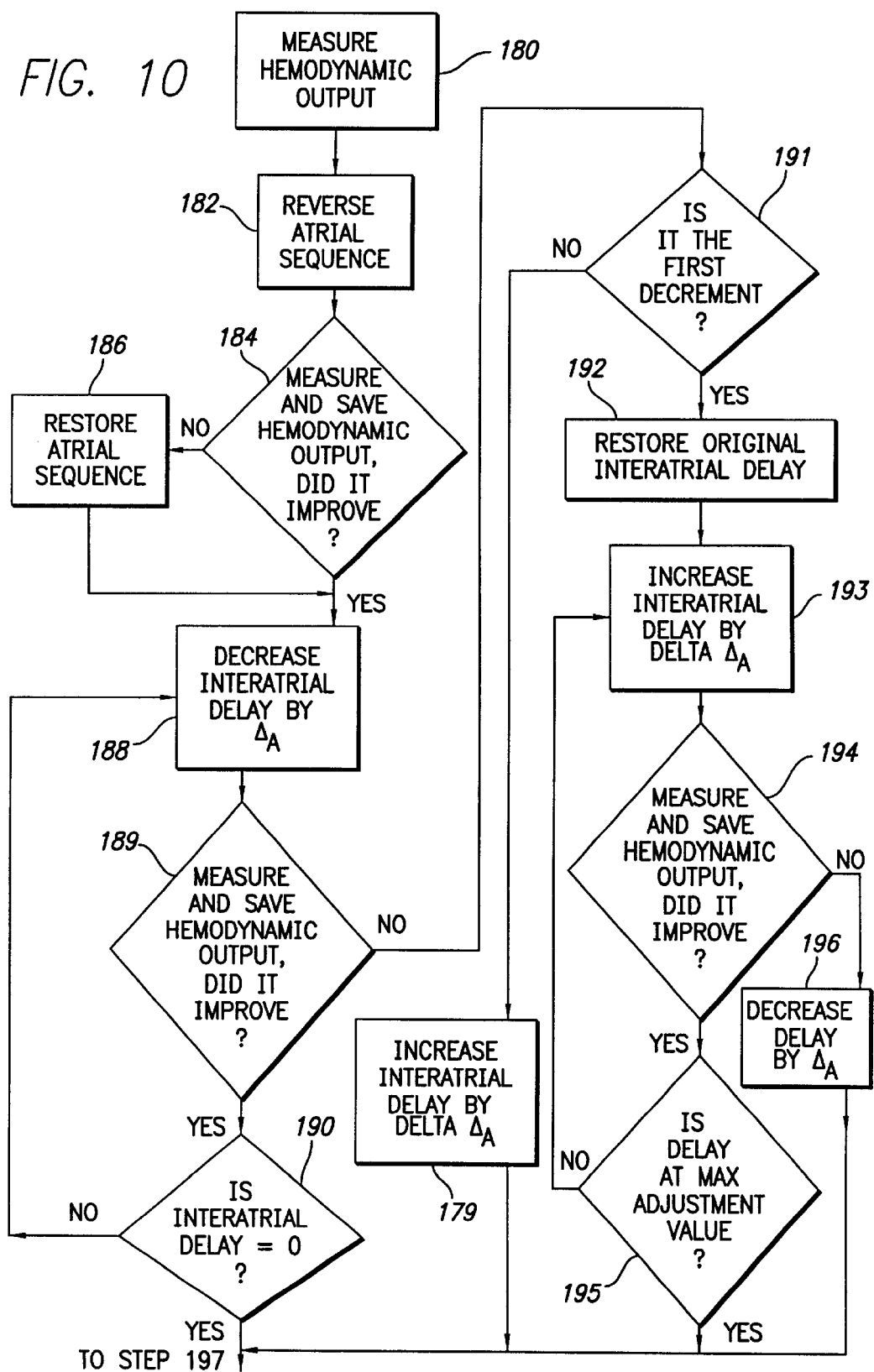
FIGS. 10 and 11 shows an a simplified flow chart of an exemplary process for optimizing the hemodynamics of the patient's heart during the ATP treatment by altering the delivered pacing sequence and/or the interchamber delays relative to the measured interval template.
Figure 11:
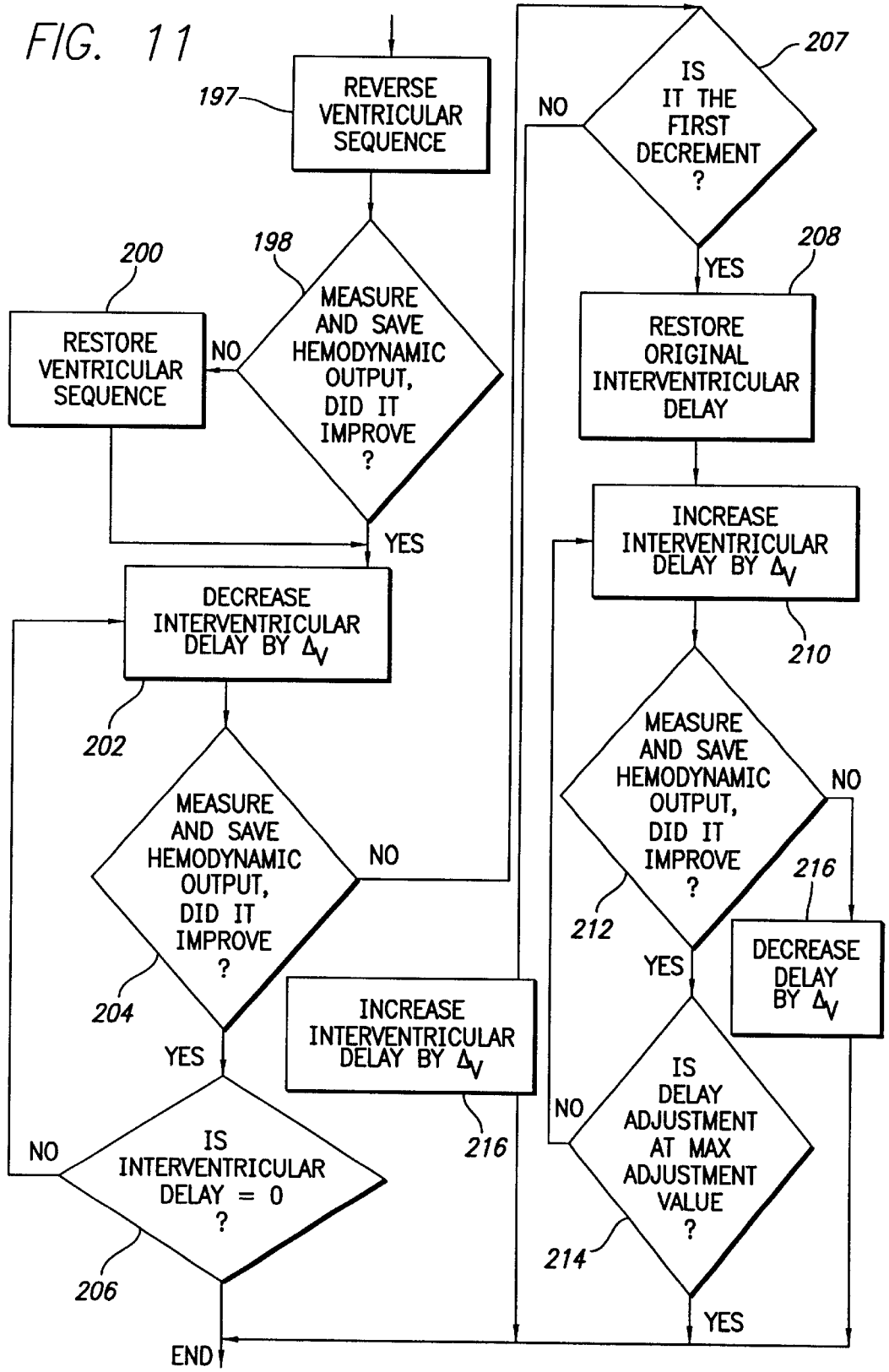

FIGS. 10 AND 11 show an a simplified flow chart of an exemplary process for optimizing the hemodynamics of the patient's heart during the ATP treatment by modifying the cardiac interval template by altering the pacing sequence and/or the interchamber delays. By measuring the hemodynamic output of the heart using a sensor, e.g., the physiologic sensor 108, the impedance measuring circuit 112, or other sensor as is known in the art that can provide an output indicative of the hemodynamic output of the patient's heart, the pacing sequence may be altered to optimize the hemodynamics of the patient's heart during the treatment for the detected tachycardia. Initially in step 180, the hemodynamic output of the patient's heart is measured to obtain a reference point. Then, in step 182, the atrial pacing sequence (e.g., right atrium before left atrium) as prescribed by the sampled interval template 128 is reversed. In step 184, the hemodynamic output is again measured and compared to the initial output measured in step 180. If an improvement is found, then the reversed atrial sequence is retained. Otherwise, the original atrial pacing is sequence is restored in step 186.

Optionally, this process is further refined in step 188 where the interchamber delay between the atria is initially reduced by a predetermined amount (e.g., by $\Delta_A$) to determine if such a change will further optimize the hemodynamic output. In step 189, the hemodynamic output is again measured and if the hemodynamic output has improved, the reduction process continues (providing that the delay has not reached zero, as determined in step 190).

If the hemodynamics did not improve, it is determined in step 191 if this lack of improvement occurred at the first decrement, i.e., there was no hemodynamic improvement by decreasing the interatrial delay. If it is not the first decrement at step 191, the interatrial delay is increased back to the previous value by ΔA at step 179 before the process continues to step 197 in FIG. 11.

If, on the other hand, this lack of improvement occurred at the first decrement (yes at block 191), then the process continues to step 192 where the interatrial delay is increased back to its original value. Next, a similar process preferably commences in steps 193–195 of increasing instead decreasing the interatrial delay in an attempt to optimize hemodynamic performance (providing that the delay has not reached a predetermined maximum value, as determined in step 195). Preferably, this optimization process continues in step 197 where the pacing sequence of the ventricles is reversed from the sensed cardiac interval template 128. In step 198, the hemodynamic output is again measured to determine if the reversed ventricular pacing sequence (e.g., left ventricle before right ventricle) has improved the hemodynamic output. If the hemodynamic output has improved, this new reversed sequence is retained. Otherwise, the original ventricular pacing sequence is restored in step 200. Preferably, this optimization continues in steps 202–216 by altering the interchamber delay between the ventricles by a prescribed value, e.g., $\Delta_V$, as long as a hemodynamic improvement occurs. This process occurs in a manner analogous to that previously described for the atria in steps 188–196.

Accordingly, what has been shown is a method and device for treating a tachycardia in a multi-chamber device. While the invention has been described by means of specific embodiments and applications thereof, it is understood that numerous modifications and variations could be made thereto by those skilled in the art without departing from the spirit and scope of the invention. For example, while it is preferable to sample and store the pre-tachycardia interval template 128, this template data may alternatively be programmed into the device 10, e.g., via the external device 102, or via default values. Additionally, the previously described algorithms may be modified to take advantage of special cases. For example, in the case of a sinus tachycardia originating from the right atrium, the interval template may be determined during the sinus tachycardia and subsequently used for treating the pathologic tachycardia. Furthermore, embodiments of the present invention may store (in memory 94) the last set of template values that terminated a tachycardia from a particular chamber, preferably stored relative to the originating chamber and/or range bins of tachycardia rates, and such embodiments then use this stored setting corresponding to the sensed tachycardia as an initial setting for the multi-chamber ATP pacing. (see for example, U.S. Pat. No. 5,144,947 for an example in a single chamber ATP environment; said patent being incorporated herein by reference in its entirety.) Finally, while this description has specifically addressed an embodiment which scales the interval template downward and thus increases the pacing rate, the use of a synchronized multi-chamber interval template with other ATP techniques is also considered to be within the scope of the present invention. It is therefore to be understood that within the scope of the claims, the invention may be practiced otherwise than as specifically described herein.

What is claimed is:

1. An implantable cardiac stimulation device configured for controlling a plurality of chambers of a patient's heart through a plurality of electrodes adapted to be implanted in a respective chamber of the heart, the stimulation device comprising:

pulse generating circuitry, coupled to the plurality of electrodes, configured to independently generate stimulation pulses to stimulate an associated heart chamber;

sensing circuitry, coupled to the plurality electrodes, configured to independently receive intrinsic cardiac signals from an associated heart chamber;

wherein the sensing circuit detects an intrinsic activation sequence and associated interchamber time delays;

a controller, coupled to the pulse generating circuitry and the sensing circuitry, configured to control the stimulation of each respective heart chamber, to detect the presence of tachycardia from the received intrinsic signals, and to determine which one of the chambers originated the tachycardia; and wherein, in response to detecting tachycardia, the controller controls a sequence of stimulation pulses according to a predetermined anti-tachycardia pacing cycle length to the controlled chambers relative to the intrinsic chamber activation sequence and the associated interchamber time delays.

2. The implantable cardiac stimulation device of claim 1, wherein the controller controls the sequence of stimulation pulses by initially delivering the sequence of stimulation pulses relative to an intrinsic cardiac signal from the chamber which originated the tachycardia.

3. The implantable cardiac stimulation device of claim 1, wherein the cardiac stimulation device is further configured to control four chambers and wherein the controlled chambers comprise the patient's right atrium, right ventricle, left atrium and left ventricle.

4. The implantable cardiac stimulation device of claim 1, wherein the controller is further configured to periodically determine the intrinsic chamber activation sequence and the associated time delays for the controlled chambers of the patient's heart.

5. The implantable cardiac stimulation device of claim 4, wherein the controller is further configured to periodically determine the intrinsic chamber activation sequence and associated interchamber time delays during a time period without pathologic tachycardia.

6. The implantable cardiac stimulation device of claim 1, wherein:

the controller is further configured to determine the absence or presence of tachycardia by periodically determining an intrinsic cardiac cycle length for one or more cardiac cycles in each of the controlled chambers and comparing each intrinsic cardiac cycle length to a predetermined tachycardia threshold cycle length; and the presence of tachycardia is indicated when the intrinsic cardiac cycle length is less than the predetermined tachycardia threshold cycle length and the absence of tachycardia is indicated when the intrinsic cardiac cycle length is greater than the predetermined tachycardia threshold cycle length.

7. The implantable cardiac stimulation device of claim 6, further comprising delivery time delays related to the associated interchamber time delays, wherein:

the controller, in response to detecting tachycardia, controls the sequence of stimulation pulses according to calculated anti-tachycardia pacing cycle lengths to the controlled chambers according to a delivery activation sequence related to the intrinsic chamber activation sequence and according to the delivery time delays.

8. The implantable cardiac stimulation device of claim 7, wherein the anti-tachycardia pacing cycle lengths is a percentage of the determined intrinsic cardiac cycle length.

9. The implantable cardiac stimulation device of claim 7, additionally comprising:

a hemodynamic sensor for monitoring the performance of the patient's heart; and wherein the controller is configured to adaptively alter the delivery activation sequence in response to changes in the monitored hemodynamic performance of the patient's heart.

10. The implantable cardiac stimulation device of claim 7, additionally comprising:

a hemodynamic sensor for monitoring the performance of the patient's heart; and wherein the controller is configured to adaptively alter the delivery time delays in response to changes in the monitored hemodynamic performance of the patient's heart.

11. A method for stimulating a patient's heart wherein the patient's heart is comprised of a plurality of chambers capable of being controlled by an implantable stimulation device, the method comprising the steps of:

periodically determining an intrinsic chamber activation sequence and associated interchamber time delays for the controlled chambers of the patient's heart;

detecting intrinsic cardiac signals from each of the controlled chambers;

determining the absence or presence of tachycardia in each of the controlled chambers in response to the intrinsic cardiac signals;

determining, in response to the presence of tachycardia, the chamber of the patient's heart which originated the tachycardia; and delivering, in response to the presence of tachycardia, a sequence of stimulation pulses to the controlled chambers of the patient's heart according to the determined intrinsic chamber activation sequence and the associated interchamber time delay, wherein the stimulation pulses are delivered according to predetermined anti-tachycardia pacing cycle lengths.

12. The method of claim 11, wherein the periodically determining step comprises the steps of:

determining suitability for determining the intrinsic chamber activation sequence by periodically looking for the absence of a tachycardia in each of the controlled chambers; and determining the intrinsic chamber activation sequence during a time period characterized by the absence of pathologic tachycardia in each of the controlled chambers.

13. The method of claim 11, wherein the step of determining the absence or presence of tachycardia comprises the steps of:

determining an intrinsic cardiac cycle length of at least one cardiac cycle for each of the controlled chambers;

comparing the intrinsic cardiac cycle length to a predetermined tachycardia threshold cycle length;

specifying the presence of tachycardia when it is determined that the intrinsic cardiac cycle length is less than the predetermined tachycardia threshold cycle length; and specifying the absence of tachycardia when it is determined that the intrinsic cardiac cycle length is greater than the predetermined tachycardia threshold cycle length.

14. The method of claim 11, wherein the delivering step comprises the step of:

determining a calculated anti-tachycardia pacing cycle length based on at least one previous tachycardia cycles;

delivering, in response to the presence of tachycardia, a sequence of stimulation pulses to the controlled chambers of the patient's heart according to the determined intrinsic chamber activation sequence and according to delivery time delays related to the determined interchamber time delays, wherein:

the sequence of stimulation pulses are delivered according to the calculated anti-tachycardia pacing cycle length; and the sequence of stimulation pulses is initially delivered relative to an intrinsic cardiac signal from the chamber which originated the tachycardia.

15. The method of claim 14, additionally comprising the steps of:

(a) monitoring hemodynamic performance of the patient's heart;

(b) adjusting one of the delivery time delays;

(c) continuing to deliver stimulation pulses using a further adjusted delivery time delay in the same direction as a previously adjusted delivery time delay if the delivery of stimulation pulses using the previously adjusted delivery time delay increases the hemodynamic performance of the patient's heart; and (d) delivering stimulation pulses according to the delivery time delay used before performing step (b) if the delivery of stimulation pulses according to the previously adjusted delivery time delay decreases the hemodynamic performance of the patient's heart.

16. The method of claim 14, additionally comprising the step of:

determining the delivery time delays by generating delivery time delay values relative to the determined interchamber time delays scaled according to the anti-tachycardia pacing cycle length.

17. The method of claim 16, additionally comprising the steps of:

(a) monitoring hemodynamic performance of the patient's heart;

(b) adjusting one of the delivery time delays;

(c) continuing to deliver stimulation pulses using a further adjusted delivery time delay in the same direction if the delivery of stimulation pulses using the previously adjusted delivery time delay increases the hemodynamic performance of the patient's heart; and (d) delivering stimulation pulses according to the delivery time delay used before performing step (b) if the delivery of stimulation pulses according to the previously adjusted delivery time delay decreases the hemodynamic performance of the patient's heart.

18. The method of claim 11, additionally comprising the steps of:

determining an intrinsic cardiac cycle length for each of the controlled chambers; and setting the anti-tachycardia pacing cycle lengths to percentages of the determined intrinsic cardiac cycle length for the chamber which originated the tachycardia.

19. The method of claim 11, wherein the delivering stimulation pulses step additionally comprising the steps of:

(a) monitoring hemodynamic performance of the patients heart;

(b) delivering stimulation pulses to the patient's heart according to a modified activation sequence wherein at least two chambers of the patient's heart are stimulated in an order opposite to that in the determined intrinsic chamber activation sequence;

(c) continuing to deliver stimulation pulses using the modified activation sequence if the delivery of stimulation pulses according to the modified activation sequence increases the hemodynamic performance of the patient's heart; and (d) delivering stimulation pulses according to the activation sequence used before performing step (b) if the delivery of stimulation pulses according to the modified activation sequence decreases the hemodynamic performance of the patient's heart.

20. The method of claim 19, additionally comprising the steps of:

(e) monitoring hemodynamic performance of the patient's heart;

(f) adjusting one of the delivery time delays;

(g) continuing to deliver stimulation pulses using a further adjusted delivery time delay in the same direction if the delivery of stimulation pulses using the previously adjusted delivery time delay increases the hemodynamic performance of the patient's heart; and (h) delivering stimulation pulses according to the delivery time delay used before performing step (f) if the delivery of stimulation pulses according to the previously adjusted delivery time delay decreases the hemodynamic performance of the patient's heart.

21. An implantable cardiac stimulation device configured for controlling a plurality of chambers of a patient's heart through a plurality of electrodes implanted in electrical contact with each of the controlled chambers, the stimulation device comprising:

means for delivering a stimulation pulse to each of the controlled chambers of the patient's heart;

means for receiving intrinsic cardiac signals from each controlled cardiac chamber;

wherein the means for receiving intrinsic cardiac signals detects an intrinsic activation sequence and associated interchamber time delays means for determining the presence of tachycardia from the intrinsic cardiac signals;

means for determining anti-tachycardia pacing cycle lengths in response to the presence of tachycardia;

means for determining which chamber originated the tachycardia; and means for delivering a sequence of stimulation pulses according to a calculated anti-tachycardia pacing cycle length to each of the controlled chambers relative to the intrinsic chamber activation sequence and the associated interchamber time delays, wherein the sequence of stimulation pulses are delivered in response to the presence of tachycardia and the sequence of stimulation pulses is initially delivered relative to an intrinsic cardiac signal of the chamber which originated the tachycardia.

22. The implantable cardiac stimulation device of claim 21, further comprising:

means to periodically determine the intrinsic chamber activation sequence and associated interchamber time delays for the controlled chambers of the patient's heart.

23. The implantable cardiac stimulation deliver of claim 21, additionally comprising:
   means for monitoring the hemodynamic performance of the patient's heart;
   means to adaptively alter a delivery activation sequence used for stimulating the controlled chambers of the patient's heart in response to changes in the monitored hemodynamic performance of the patient's heart; and
   means for determining the delivery activation sequence based on the intrinsic chamber activation sequence.

24. The implantable cardiac stimulation deliver of claim 21, additionally comprising:
   means for monitoring the hemodynamic performance of the patient's heart;
   means to adaptively alter a delivery interchamber delay used for controlling a time delay between stimulating two of the controlled chambers of the patient's heart in response to changes in the monitored hemodynamic performance of the patient's heart; and
   means for determining the delivery interchamber delay based on one of the intrinsic interchamber delays.

* * * * *